(12) United States Patent
Shi et al.

(10) Patent No.: US 8,126,235 B2
(45) Date of Patent: Feb. 28, 2012

(54) METHODS AND APPARATUS FOR AUTOMATED BASE-CALLING ON MULTIPLE DNA STRANDS

(75) Inventors: Xiaomeng Shi, West Roxbury, MA (US); Muriel Medard, Belmont, MA (US); Ralf Koetter, Munich (DE); Nuala Ann Koetter, legal representative, Munich (DE); Desmond S. Lun, Mawson Lakes (AU)

(73) Assignee: Massachusetts Institute of Technology, Cambridge, MA (US)

( * ) Notice: Subject to any disclaimer, the term of this patent is extended or adjusted under 35 U.S.C. 154(b) by 500 days.

(21) Appl. No.: 12/418,933

(22) Filed: Apr. 6, 2009

(65) Prior Publication Data

US 2010/0074492 A1 Mar. 25, 2010

Related U.S. Application Data

(60) Provisional application No. 61/123,025, filed on Apr. 4, 2008.

(51) Int. Cl.
*G06K 9/00* (2006.01)
(52) U.S. Cl. .......................... 382/129; 382/128; 382/130
(58) Field of Classification Search .......... 382/128–130, 382/182–183, 185, 224, 229, 209
See application file for complete search history.

(56) References Cited

U.S. PATENT DOCUMENTS

| | | | | |
|---|---|---|---|---|
| 5,853,979 A | * | 12/1998 | Green et al. | 435/5 |
| 6,404,907 B1 | * | 6/2002 | Gilchrist et al. | 382/129 |
| 7,222,059 B2 | * | 5/2007 | Izmailov et al. | 703/2 |

* cited by examiner

*Primary Examiner* — Marcos D Pizarro Crespo
*Assistant Examiner* — Sue Tang
(74) *Attorney, Agent, or Firm* — Wolf, Greenfield & Sacks, P.C.

(57) ABSTRACT

In some aspects, a method of automated base-calling using at least one image obtained from a chemical sequencing process performed simultaneously on a plurality of DNA strands, the at least one image including intensity information corresponding to locations of at least one base in the plurality of DNA strands is provided. The method comprises processing the at least image to obtain a function corresponding to the intensity information in the at least one image for the at least one base, the function incorporating intensity information corresponding to each of the plurality of DNA strands, identifying a plurality of peaks in the function, the plurality of peaks indicating possible locations for the at least one base in the plurality of DNA strands, assigning membership to each of the plurality of peaks by determining whether each of the plurality of peaks is believed to have resulted from none, one or multiple of the plurality of DNA strands, and computing a sequence for the at least one base for each of the plurality of DNA strands based, at least in part, on the membership assignment.

20 Claims, 9 Drawing Sheets

METHODS AND APPARATUS FOR AUTOMATED BASE-CALLING ON MULTIPLE DNA STRANDS

CROSS-REFERENCE TO RELATED APPLICATION

This application claims the benefit under 35 U.S.C. §119(e) of U.S. Provisional Application 61/123,025, filed Apr. 4, 2008, entitled "METHODS AND APPARATUS FOR AUTOMATED BASE-CALLING ON MULTIPLE DNA STRANDS," which is incorporated herein in its entirety.

TECHNICAL FIELD

The present disclosure relates to automated base calling for sequencing DNA.

BACKGROUND

Sanger sequencing is a widely used chemical process for DNA sequencing. In Sanger sequencing, a single strand of DNA is replicated using a chain-termination method, which typically involves a reaction of the single-stranded DNA with a DNA primer and DNA polymerase that together perform DNA replication. Fluorescently labeled nucleotides specific to each of the four nucleotide base types, Adenosine, Cytosine, Guanine and Thymine (A, C, G, T), may be included in the reactions. The DNA sample may be divided into four separate sequencing reactions, containing the four standard deoxynucleotides (dATP, dGTP, dCTP and dTTP) and the DNA polymerase. To each reaction is added one of the four dideoxynucleotides (ddATP, ddGTP, ddCTP, or ddTTP). These dideoxynucleotides are chain-terminating nucleotides that cause DNA replication to be terminated by the incorporation of the chain-terminating nucleotides, resulting in strand fragments of different lengths.

The resulting fragments may be electrophoretically separated through gels or capillaries by length, which is inversely proportional to their traveling speed. As a result, the fragments move through the gel or capillary in order from shortest length to longest length. A laser or other excitation source may be positioned proximate the capillary to excite the fluorescently labeled nucleotides. Optical detection equipment may likewise be positioned to detect the fluorescence from the excited chain-terminating nucleotides to categorize the nucleotides into the four base-types. The optical detection equipment may capture the fluorescence emitted by the excited nucleotides as an image, such as a chromatogram. Because the fragments are ordered by length and pass the optical equipment in sequence from shortest fragments to longest fragments, the order of the base-types of the DNA sequence is encoded as a function of time. Each of the four DNA synthesis reactions is run in one of four individual "lanes" corresponding to the four base types A, C, G and T and the pattern of fluorescence of the excited nuclei may he captured as an image and recorded.

There are many techniques using gel electrophoresis, capillary electrophoresis and other methods that are suitable for obtaining an image corresponding to a DNA sequence. For example, some techniques include adding four different dyes associated with respective ones of the four base types into a single reaction or chemical sequencing process. It should be appreciated that the base-calling techniques described herein may be used with any suitable method of obtaining one or more DNA sequence images, as the aspects of the invention are not limited to any particular chemical sequencing process or method of image acquisition.

Figure 1:
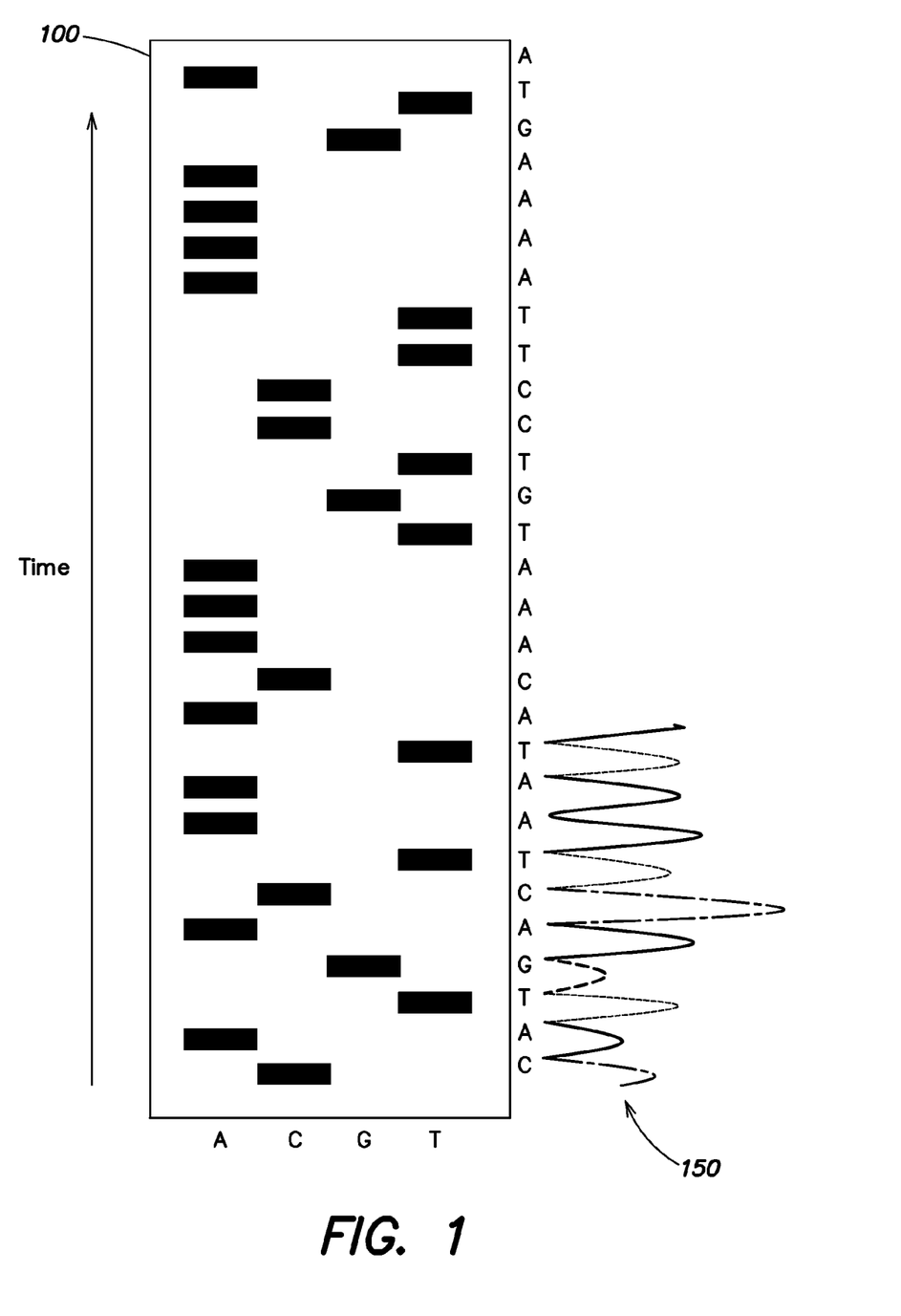
FIG. 1 illustrates a schematic of an image captured using a chemical sequencing process on which various methods described herein may be applied to perform automated base-calling.

FIG. 1 illustrates a schematic of an image captured using the above described process. In image 100, the dark bands correspond to fragments of different lengths. A dark band in a lane indicates a fragment that is the result of chain termination after incorporation of the respective one of the chain-terminating nucleotides (ddATP, ddGTP, ddCTP, or ddTTP). The terminal nucleotide base can be identified according to which dideoxynucleotide was added in the reaction giving that band. The relative positions of the different bands among the four lanes are then used to read (from bottom to top) the DNA sequence as indicated. It should be appreciated that image 100 is schematic and the dark bands in actual images will vary in intensity.

The process of extracting the DNA sequence from the image is referred to herein as "base-calling." Manual base calling is tedious and time-consuming and prone to human error. To expedite this process, many automatic methods have been developed to process the images and extract the sequence of bases. For example, Phred is a widely used algorithm for base calling a single sequence captured on various standard types of image formats. Parametric deconvolution, Kalman prediction with dynamic programming, and Markov Monte Carlo methods have all been used for single strand base-calling.

As discussed above, the intensity of the dark bands varies over the domain of the band. In general, the shape of the intensity variation (which corresponds to concentration) ramps up exponentially to a peak value and then decays in a similar fashion. Accordingly, processing an x-ray or gel image may include extracting four time varying signals corresponding to each of the four base types, respectively. Signal 150 shown in FIG. 1 illustrates the four time-varying signals together, with the different base types (identified by the "lane" position of the corresponding band) denoted using different line patterns. From the time-varying signals, the DNA sequence may be determined. The time-varying signals extracted from an image are individually referred to herein as a "trace."

It should be appreciated that time-varying signal 150 is an idealized extraction. Actual signals are typically degraded from base-line noise, amplitude variation, increasing pulse widths which deteriorates peak resolutions, jitter in peak spacings which contributes to inter-symbol interference (ISI), etc.

SUMMARY

Some embodiments include a method of automated base-calling using at least one image obtained from a chemical sequencing process performed simultaneously on a plurality of DNA strands, the at least one image including intensity information corresponding to locations of at least one base in the plurality of DNA strands, the method comprising processing the at least image to obtain a function corresponding to the intensity information in the at least one image for the at least one base, the function incorporating intensity information corresponding to each of the plurality of DNA strands, identifying a plurality of peaks in the function, the plurality of peaks indicating possible locations for the at least one base in the plurality of DNA strands, assigning membership to each of the plurality of peaks by determining whether each of the plurality of peaks is believed to have resulted from none, one or multiple of the plurality of DNA strands, and computing a sequence for the at least one base for each of the plurality of DNA strands based, at least in part, on the membership assignment.

Some embodiments include a computer readable medium having processor-executable instructions stored thereon, the processor-executable instruction, when executed by at least one processor, performing a method of automated base-calling using at least one image obtained from a chemical sequencing process performed simultaneously on a plurality of DNA strands, the at least one image including intensity information corresponding to locations of at least one base in the plurality of DNA strands, the method comprising processing the at least image to obtain a function corresponding to the intensity information in the at least one image for the at least one base, the function incorporating intensity information corresponding to each of the plurality of DNA strands, identifying a plurality of peaks in the function, the plurality of peaks indicating possible locations for the at least one base in the plurality of DNA strands, assigning membership to each of the plurality of peaks by determining whether each of the plurality of peaks is believed to have resulted from none, one or multiple of the plurality of DNA strands, and computing a sequence for the at least one base for each of the plurality of DNA strands based, at least in part, on the membership assignment.

Some embodiments include an apparatus for performing automated base-calling using at least one image obtained from a chemical sequencing process performed simultaneously on a plurality of DNA strands, the at least one image including intensity information corresponding to locations of at least one base in the plurality of DNA strands, the apparatus comprising an input to receive the at least one image, and at least one controller configured to process the at least image to obtain a function corresponding to the intensity information in the at least one image for the at least one base, the function incorporating intensity information corresponding to each of the plurality of DNA strands, identify a plurality of peaks in the function, the plurality of peaks indicating possible locations for the at least one base in the plurality of DNA strands, assigning membership to each of the plurality of peaks by determining whether each of the plurality of peaks is believed to have resulted from none, one or multiple of the plurality of DNA strands, and compute a sequence for the at least one base for each of the plurality of DNA strands based, at least in part, on the membership assignment.

Some embodiments include a method for base-calling a plurality of strands of DNA simultaneously, the method comprising obtaining a composite trace of the DNA strands, the composite trace having an individual trace for each of the plurality of strands of DNA, estimating a plurality of sets of peak parameters for the composite trace, and assigning each of the plurality of sets to one or a combination of the individual traces forming the composite trace.

Some embodiments include estimating the plurality of sets of peak parameters by modeling the composite trace and minimizing the error between the model and the composite trace. Some embodiments include assigning each of the plurality of sets by forming a global function describing the composite trace, factoring the global function into a product of local functions, representing the factorization as a factor graph, applying a Sum-Product Algorithm to the factor graph to associate each of the plurality of sets with one or a combination of the individual traces forming the composite trace.

Some embodiments include a method for base-calling a plurality of strands of DNA simultaneously, the method comprising obtaining a composite trace of the DNA strands, the composite trace having an individual trace for each of the plurality of strands of DNA and being composed of a plurality of peaks, modeling the composite trace as a global function, factoring the function into a product of local functions, representing the factorization as a factor graph, applying a Sum-Product Algorithm to the factor graph to associate each of the plurality of peaks with one or a combination of the individual traces forming the composite trace.

DETAILED DESCRIPTION

The Sanger method, while considered the most efficient method of DNA sequencing and therefore generally the method of choice, is relatively time consuming. A typical run, which requires more than 30 minutes to complete, gives approximately six to eight hundred bases, corresponding to 7,000 to 10,000 sample points. Given that genomes may contain millions of bases and repetition may be required to achieve high accuracy in subsequent assembly, significant time is required to sequence a single genome. In addition, the cost of the apparatus and the reagents used in the reaction may be substantial. Applicant has appreciated that one bottleneck in the process is the requirement that only a single DNA strand be sequenced at a time. Current sequencers are unable to perform base-calling on traces of more than a single strand of DNA.

Applicant has developed methods and apparatus for sequencing multiple DNA strands simultaneously. In some embodiments, automatic base-calling is performed on superposed or composite traces from multiple DNA strands. By base-calling on multiple strands simultaneously, the time required to sequence a genome or other nucleic acid molecule can be approximately divided by N, where N is the number of strands for which base-calling is performed simultaneously.

Following below are more detailed descriptions of various concepts related to, and embodiments of, methods and apparatus according to the present invention. It should be appreciated that various aspects of the invention described herein may be implemented in any of numerous ways. Examples of specific implementations are provided herein for illustrative purposes only. While the Sanger method has been described as an exemplary method by which images of fluorescence patterns of nucleotides are obtained, embodiments described herein may be performed on any type of image, obtained using any method, from which traces can be extracted, as the aspects of the invention are not limited in this respect.

Figure 2A:
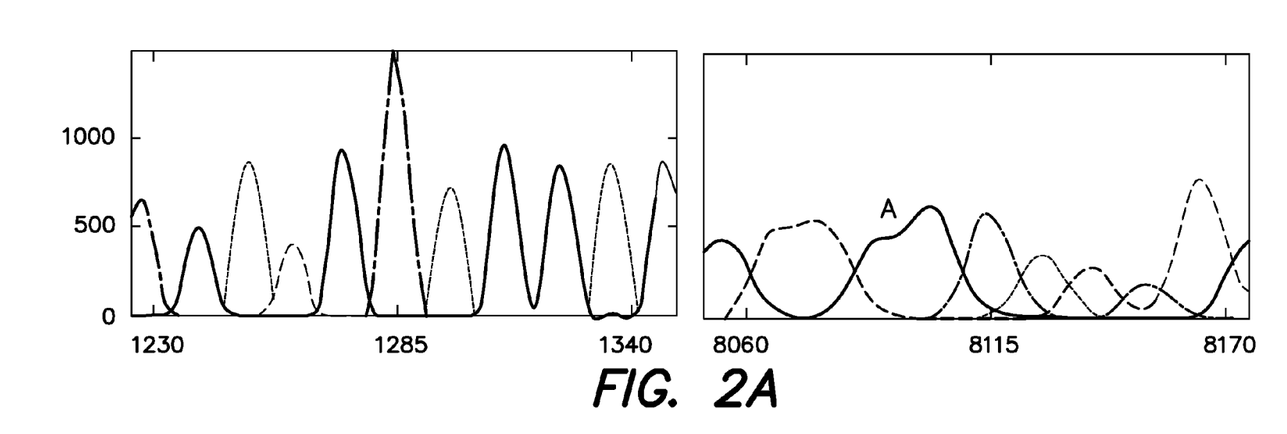
FIG. 2A illustrates a portion of a trace from an experiment using only a single strand of DNA.
Figure 2B:
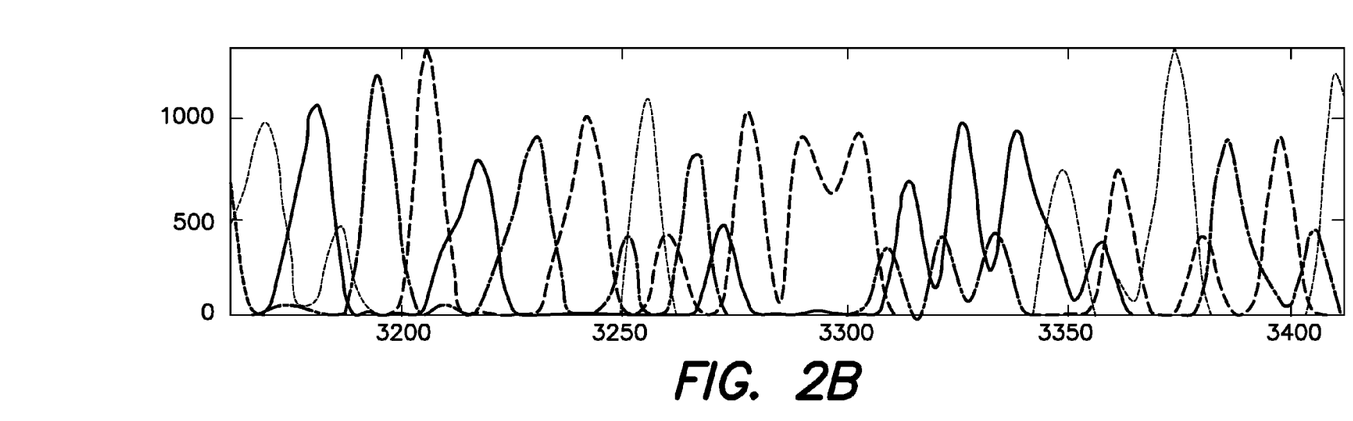
FIG. 2B illustrates a portion of a trace from an experiment using two DNA strands simultaneously, in accordance with some embodiments.

FIGS. 2A and 2B illustrate a portion of a trace from an experiment using only a single strand of DNA, and an experiment using two DNA strands simultaneously, respectively. FIG. 2A illustrates two portions of the trace. The first portion illustrates the trace from samples 1230 to 1340 (e.g., samples relatively near the beginning of the trace). The second portion illustrates the trace from samples 8050 to 8170, showing the deterioration of peak resolution due to increasing pulse widths that occurs towards the end of the trace. FIG. 2B illustrates a composite trace comprised of a first trace (referred to as the major trace) and a second trace (referred to as the minor trace), obtained from first and second DNA strands, respectively, that were simultaneously imaged from the same reactions.

As compared to the single-strand trace, the composite trace is relatively complicated, increasing the complexity of base-calling on the composite trace. In particular, the multiple traces are not synchronized in time and the superposition of the traces renders it difficult to ascertain the respective contributions of the major and minor traces. Conventional single strand automated sequencers rely on the assumption that there exists a measure of uniformity in the peaks. This assumption is not valid for multiple strand sequences because the multiple strands are not aligned in time. Therefore, single strand methods cannot be extended to handle cases where multiple DNA strands are simultaneously sequenced. As shown in FIG. 2B, the average amplitudes of the major and minor traces are different and can be distinguished. Controlling the amplitudes of the traces can be accomplished by controlling the concentrations of the reagents used in the reactions. The amplitude differences assist in determining which trace a particular peak belongs to, and facilitates accurate base-calling of multiple DNA strands.

Figure 3:
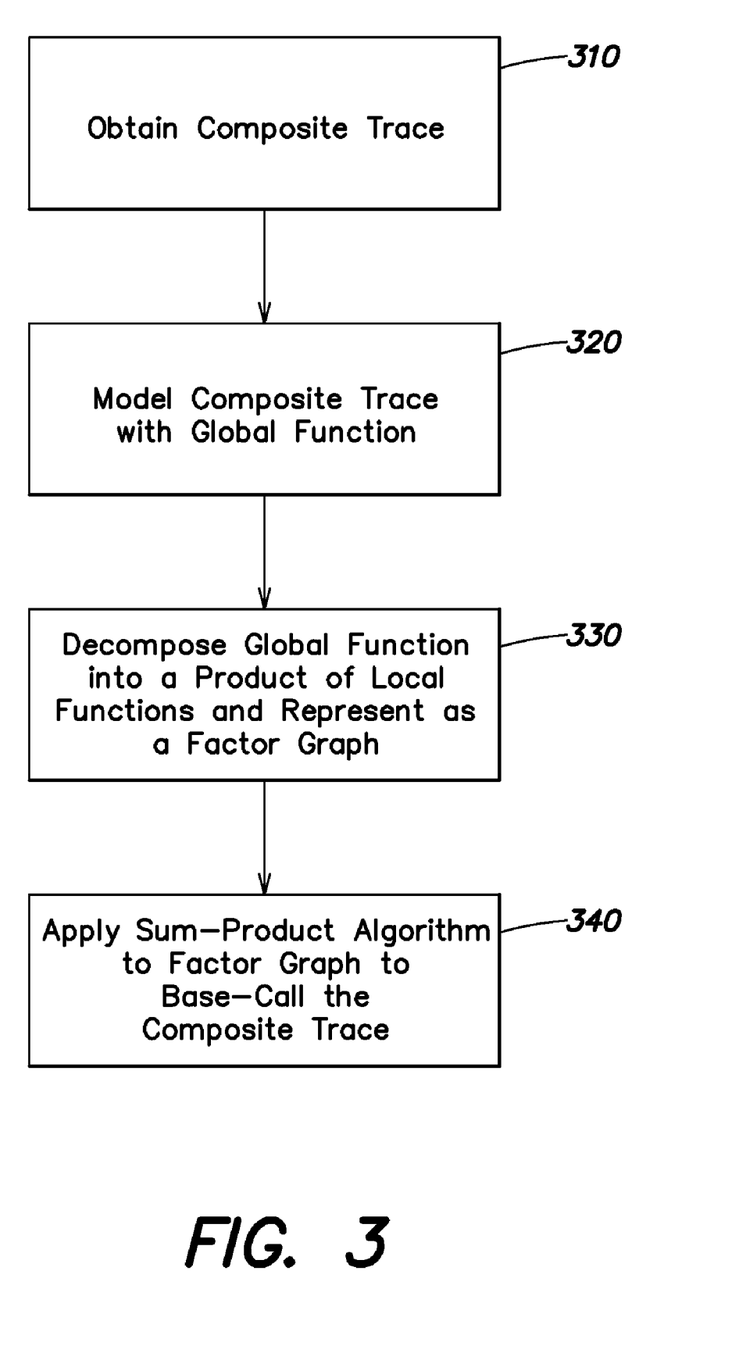
FIG. 3 illustrates a method of performing automatic sequencing of multiple strands of DNA simultaneously, in accordance with some embodiments.

FIG. 3 illustrates a method of performing automatic sequencing of multiple strands of DNA simultaneously, in accordance with some embodiments. In act 310, a composite trace comprised of traces corresponding to multiple DNA strands is obtained. The composite trace may be obtained using any suitable image processing algorithm capable of sampling an image of a DNA sequencing experiment using multiple strands of DNA. In act 320, the composite trace is modeled as a global function having parameters that describe each of the composite traces. In act 330, the global function is decomposed into a product of local functions and represented by a factor graph. In act 340, a Sum-Product algorithm is applied to the factor graph to classify each peak in the composite trace as belonging to one of the multiple component traces.

Some embodiments of the above method are described in further detail below in connection with an exemplary experiment in which a composite trace extracted from an image comprising the superposition of traces from two respective DNA strands. It should be appreciated, however, that the algorithms described herein may be extended to more than two simultaneous DNA strands. As discussed above, the amplitude of the peaks in the traces relates to the concentration of fragments at the associated length. The amplitude (concentrations) can be approximately controlled by administering the appropriate concentration of reagent in the reaction. In particular, the amplitude ratio between a first and a second of the DNA strands can be approximately controlled by the respective concentration of the reagent used in the reaction. The major trace refers herein to the higher amplitude trace and the minor trace refers to the lesser amplitude trace. One exemplary amplitude ratio is approximately 2 between the major and minor trace, although any other suitable ratio may be used.

A first step may include modeling the composite trace as a global function. A sampling of the time-varying joint trace (e.g., a trace of which a portion is schematically illustrated in FIG. 2A) extracted from an image of a DNA sequencing experiment may be described as follows:

$$y(t) = \sum_{i=1}^{N_1} \alpha_{1i} p(t - \tau_{1i}) x_{1i} + \sum_{j=1}^{N_2} \alpha_{2j} p(t - \tau_{2j}) x_{2j} + e(t), \quad (1)$$

where the first summation represents the major trace and the second summation represents the minor trace. In equation 1, $N_1$ and $N_2$ are the number of peaks in the major and minor traces, respectively, $\alpha_1$ and $\alpha_2$ are the amplitudes associated with the respective peaks, $\tau_1$ and $\tau_2$ are the location of the respective peaks, and p(t) is a generic pulse shape. In addition, $x_1$ and $x_2$ take on one of four codewords corresponding to the four base types (e.g., {0001, 0100, 0010, 0001}), and e is additive noise. Applicant has appreciated from experimental data that for each sequence, the peak amplitudes are approximately independent, identically distributed with a Gamma distribution, and the peak timing locations are first order Markov, in the sense that the conditional distribution $f(\tau_{l,i+1}|\tau_{l,i})$ satisfies, $$f(\tau_{l,i+1}|\tau_{l,i}) = \theta_{\Delta\tau}(\tau_{l,i+1} - \tau_{l,i}) \; l \in \{1,2\}, \quad (2),$$

where $f_{\Delta\tau}$ has a mean equal to the slowly varying average peak spacing, and a standard deviation of less than two samples. The additive noise e is assumed to be white Gaussian, with zero mean and standard deviation $\sigma_e$. This model allows the dependencies to be represented by a factor graph. A factor graph is a graphical model that represents a generic function f. A factor graph is a bipartite graph in the sense that all graph nodes can be divided into two groups; the variable node and the function node. A connection (e.g., an edge) exists between a variable node and a function node if the variable is an argument of the function. Thus, the factor graph allows a relatively complex composite function to be expressed as the product of smaller local functions (i.e., functions with fewer arguments than the global function).

Figure 4:
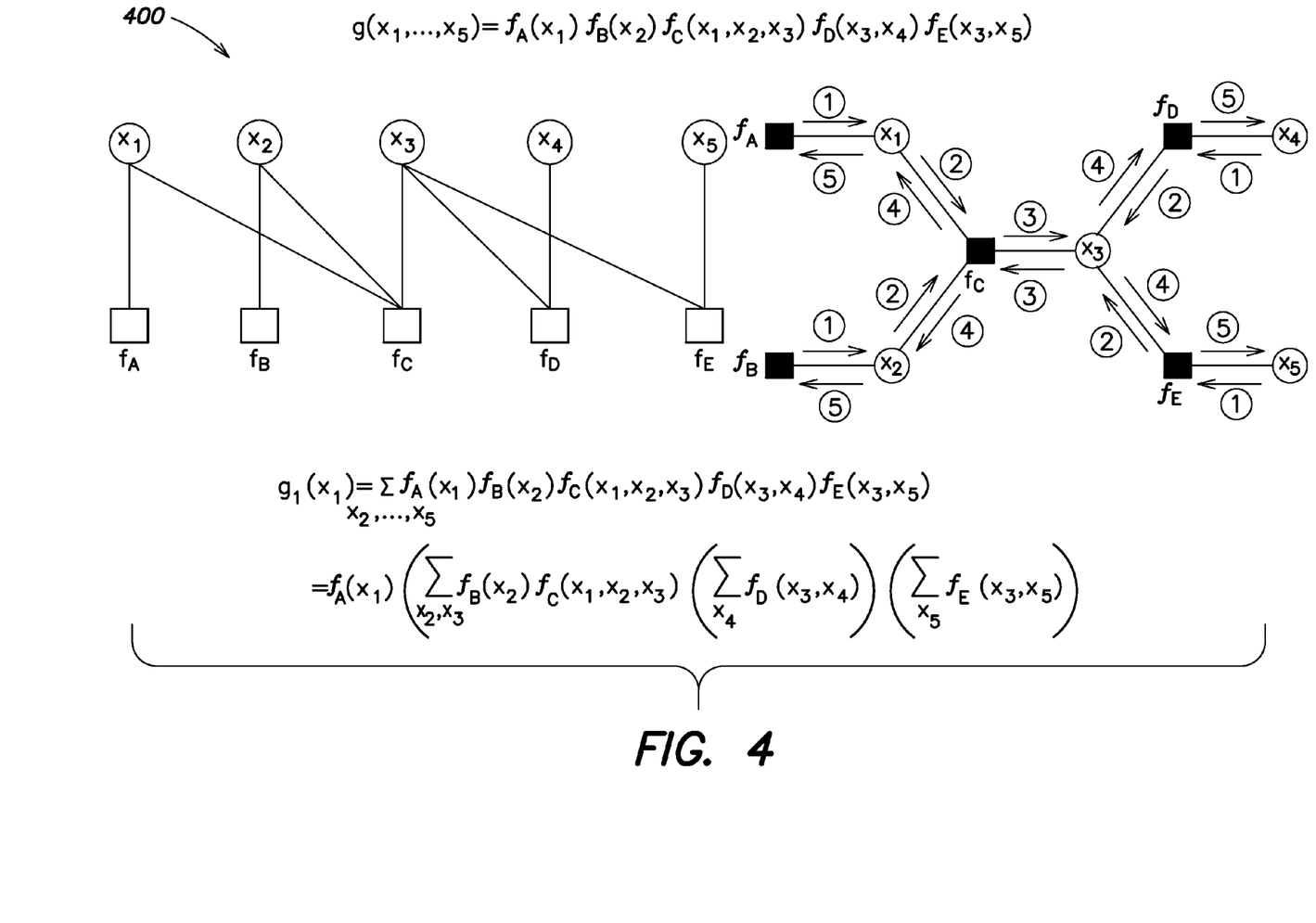
FIG. 4 illustrates various concepts related to factor graphs.

FIG. 4 illustrates a simple example of a factor graph. In FIG. 4, a function $g(x_1, \ldots, x_5)$ has been factored into a product of smaller functions. Though g is relatively simple in this example, this can be viewed as decomposing a relatively complex global function into a product of local functions. The factor graph 400 represents this factorization. In a factor graph, the circles represent the variable nodes (i.e., the arguments of the function) and the square nodes represent the function nodes. As shown, each function node is connected to a variable node if the variable is an argument of the function. Thus, given a global function and its factorization, a factor graph representation may be generated.

A factor graph representation may be desirable because an algorithm known as the Sum-Product Algorithm can be applied to a factor graph to compute the marginal function of each of the variables. For example, the marginal function for the variable $x_1$ is shown by the expression for $g_1(x_1)$ shown in FIG. 4. The marginal function for $x_1$ is the original function g summed over all of the other variables (i.e., summed over $x_2$, $x_3$, $x_4$ and $x_5$ in the example of FIG. 4). If g, for example, represents a probability distribution, then what results from applying the Sum-Product algorithm for a given variable is the marginal distribution for that variable. That is, from a factor graph representing a joint probability distribution of n variables, n marginal distributions (i.e., one for each variable) may be computed using the Sum-Product Algorithm.

The marginal function $g_1$ can be rewritten in a form that is related to the sum of products of the factorization function as shown by the second expression of $g_1$ shown in FIG. 4. The sum of products expression shows the order of computations of summation expressions needed in order to compute the marginal function, and is at the core of the Sum-Product Algorithm. The Sum-Product Algorithm for the sum of products expression as applied to the factor graph is illustrated to the right of the factor graph in FIG. 4. Thus, the Sum-Product Algorithm may be used to compute marginal functions for each variable in the global function by describing how to traverse the factor graph (i.e., by describing how computations are passed between nodes in the factor graph). The Sum-Product Algorithm as it applies to factor graphs is described in further detail in F. R. Kschischang, B. Frey, and H. A. Loeliger, "Factor graphs and the sum-product algorithm," *IEEE Trans. Inform. Theory*, vol. 47, no. 2, pp. 498-519, 2001, which is herein incorporated by reference in its entirety.

Figure 5:
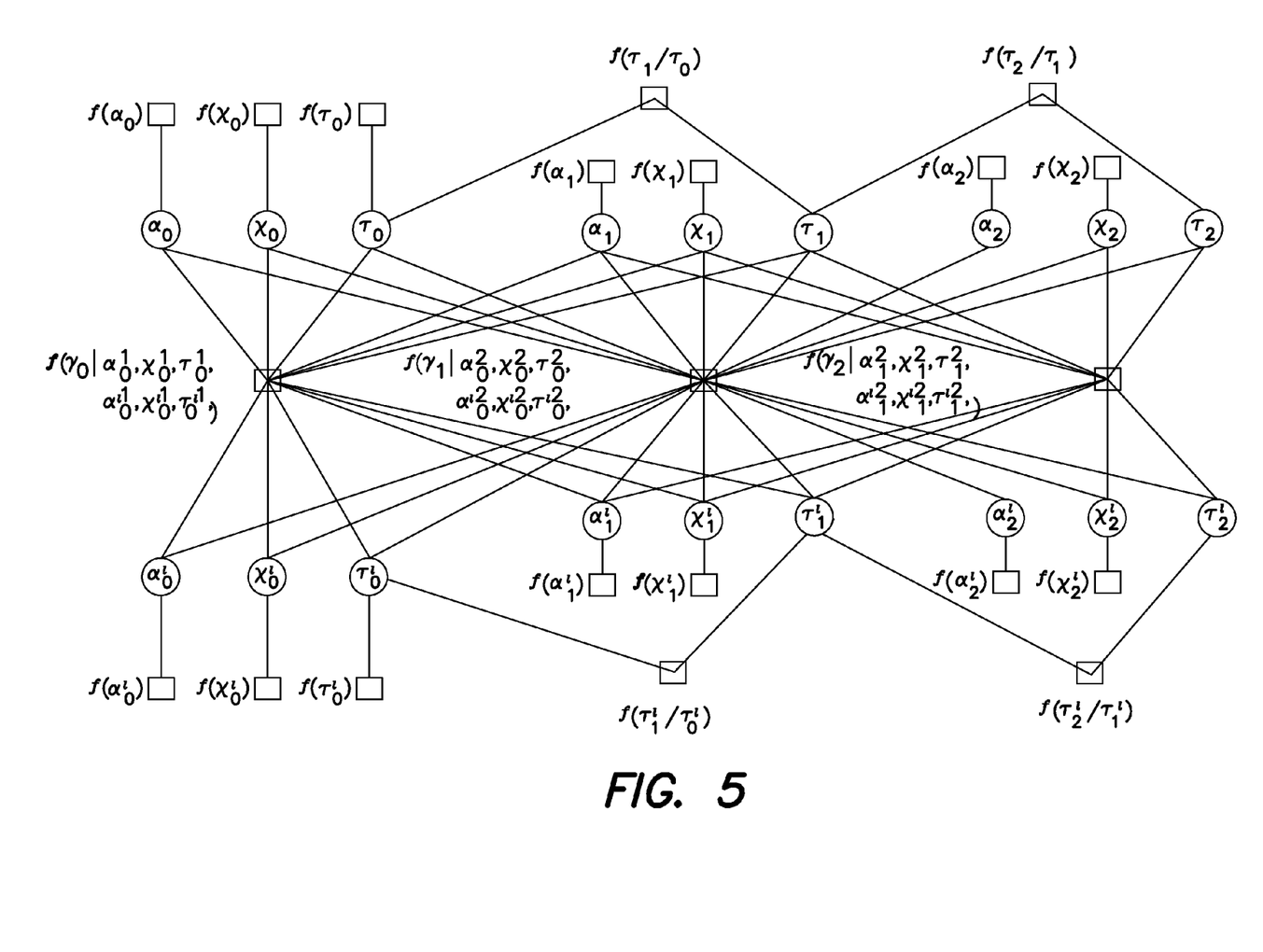
FIG. 5 illustrates a factor graph representation for a global function $y(t)$.

The factor graph representation for the global function y(t) is illustrated in FIG. 5, wherein circles represent random variables and squares represent probability distributions.

Thus, the circles represent the parameters to be estimated, of which there are three for each peak in the major and minor trace. The factor graph can be more easily understood by viewing it in its component parts. First, the factor graph can viewed as having a top portion associated with the major trace and a bottom portion associated with the minor trace. Thus, the top circles represent the parameters of the major sequence and the bottom circles represent the parameters of the minor sequence. A prime (') therefore, denotes the minor sequence.

The squares (i.e., the function nodes) down the center dividing the major and minor sequence represent the likelihood of the data $y_k$ given the parameters to which the associated function is connected. It should be noted that the dependency structure is first order in that only neighbors are considered. As discussed above, a factor graph can be used as a basis to apply a Sum-Product algorithm to compute marginal probabilities. Thus, the dependency structure, together with conditionals obtained from training data, allows the Sum-Product Algorithm to be applied to the factor graph for estimation of individual bases.

Applicant has appreciated that, while generally optimal, the pure factor graph solution described above may be overly complex and computationally expensive. One reason for this additional complexity and computation time is that the factor graph is composed under the assumption of near uniform alignment between the major and minor traces and hence interference is caused by adjacent peaks in both traces. However, the traces may not be aligned and information about the alignment (or misalignment) may not be known a priori. Accordingly, Applicant has developed a two-step approach to multiple strand base-calling. Some embodiments of the two-step approach include separating the operation of timing recovery and source identification.

Figure 6:
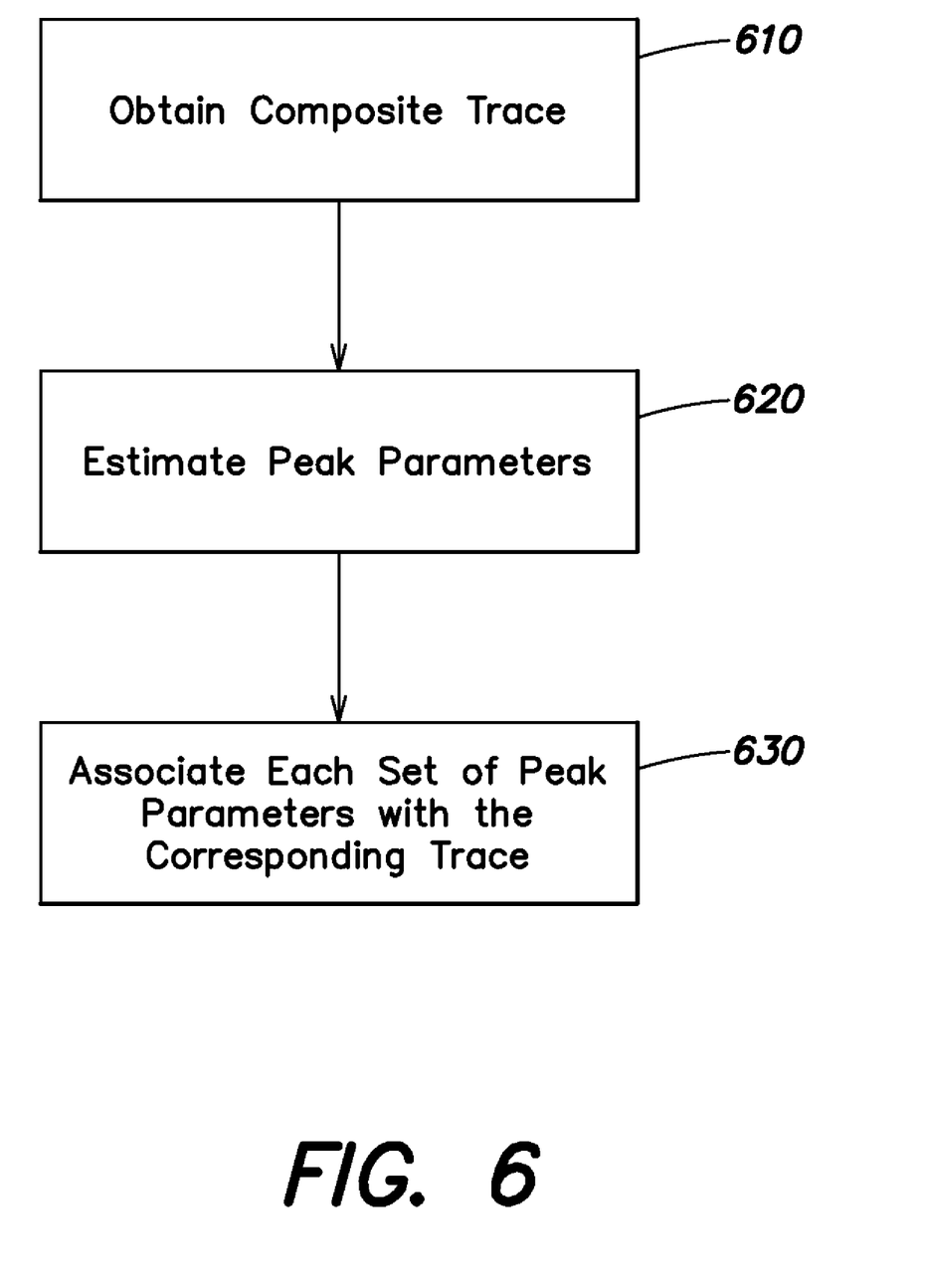
FIG. 6 illustrates a method of multiple strand base-calling, in accordance with some embodiments.

FIG. 6 illustrates a method of multiple strand base-calling, in accordance with some embodiments. In act 610, a composite trace is obtained from an image of DNA sequencing reaction using multiple DNA strands. In act 620, the parameters of the peaks in the composite trace are estimated. In act 630, each estimated set of peak parameters is labeled as corresponding to one of the traces, or some combination of multiple traces to complete the base-calling operation.

Some embodiments for performing the two-step method described in FIG. 6 are described below in connection with an exemplary experiment using two DNA strands. While the embodiments are described below in connection with joint base-calling, the algorithms may be extended to composite traces obtained from more than two DNA strands. As discussed above, automated base-calling may be split into two steps. In a first step, the timing of the sequences is recovered prior to labeling the identified peaks as belonging to the major or minor traces. That is, peak amplitudes and peak locations for the composite trace are estimated before determining which trace the peak parameters belong to. The sample time-varying signal y in Equation 1 may be viewed as the convolution product of the generic pulse p(t) and two composite spike trains, expressed as:

$$z(t) = \sum_{i=1}^{N_1} \alpha_{1i} \delta(t - \tau_{1i}) x_{1i} + \sum_{j=1}^{N_2} \alpha_{2j} \delta(t - \tau_{2j}) x_{2j} .. \quad (3)$$

Using an indicator variable in, z can be rewritten as, $$z(t) = \sum_{k=1}^{N} \alpha_k x_k \delta(t - \tau_k)[\delta(m_{k,1}) + \delta(m_{k,2}) - \delta(m_{k,1}, m_{k,2})], \quad (4)$$

where $m_k \in \{(00), (10), (01), (11)\}$, representing whether a spike at time $\tau_k$ has originated from noise, the major sequence, the minor sequence, or from both. Note that there is no reference to any indices distinguishing the two components, i.e., no distinction is made between the major trace components and minor trace components. Estimation of the values $\alpha$, x, $\tau$, and in for each base allows the two constituent sequences to be identified. The variable $m_k$ is referred to herein as the indicator variable, which ultimately is to be determined. That is, in the first step, peak amplitudes and peak locations for each base type are identified. In the second step, for each identified peak amplitude, peak location and base type, it is determined whether the peak parameter set belongs to the major trace, the minor trace or both (or noise).

Recovery of peak amplitude, timing and base type (known) information may include deconvolution of the sample data y. To achieve this, the data may be first divided into windows of 500 samples, with adjacent windows overlapping by 250 samples. From the earlier part of the trace (i.e., where pulse widths are relatively narrow), a few isolated, well defined pulses are chosen based on curvature, cumulative area, and relative amplitudes. The pulses may then be normalized to form generic pulse shape p'(t). For the l-th window, similar computations can be performed to find some well resolved pulses. However, since the ISI effect becomes more pronounced towards the end of the trace (e.g., as illustrated by the overlapping pulses illustrated in FIG. 2A), pulse shapes estimated as described above may not be representative of pulse shapes toward the end of the trace. Thus, the average full width at half maximum (FWHM) may be computed and p'(t) scaled accordingly to form $p_l'(t)$.

To deconvolve, first assume the additive noise e is white Gaussian. The following mean square minimization can be performed for each of the four base types, yielding the most likely underlying sequence:

$$\hat{\underline{\alpha}}^l, \hat{\underline{\tau}}^l = \arg\min \sum_t \left( y(t) - \sum_{k=1}^{N_l} \alpha_k \tilde{p}(t - \tau_k) \right)^2. \quad (5)$$

That is, the amplitude of the peaks and the peak locations that minimize the squared error between the composite trace and the summation expression are determined. It should be appreciated that the minimization problem expressed in equation 5 may be solved using any optimization scheme, such as gradient descent, or any other analytical or iterative methods. It should be appreciated that the composite trace is in reality four composite traces, one for each of the four base types. The four composite traces are typically processed separately. Accordingly, the minimization may be performed on each of the four composite traces, each of which are divided into l windows. The resulting data $\hat{\alpha}^1, \hat{\tau}^1$ are therefore the set of peak amplitudes, and locations of each of the peaks for the l-th window, and the output of the minimization step is the data set $\hat{\alpha}_i^1, \hat{\tau}_i^1$, where i takes on values of 1-4 corresponding to the four base types.

Figure 7:
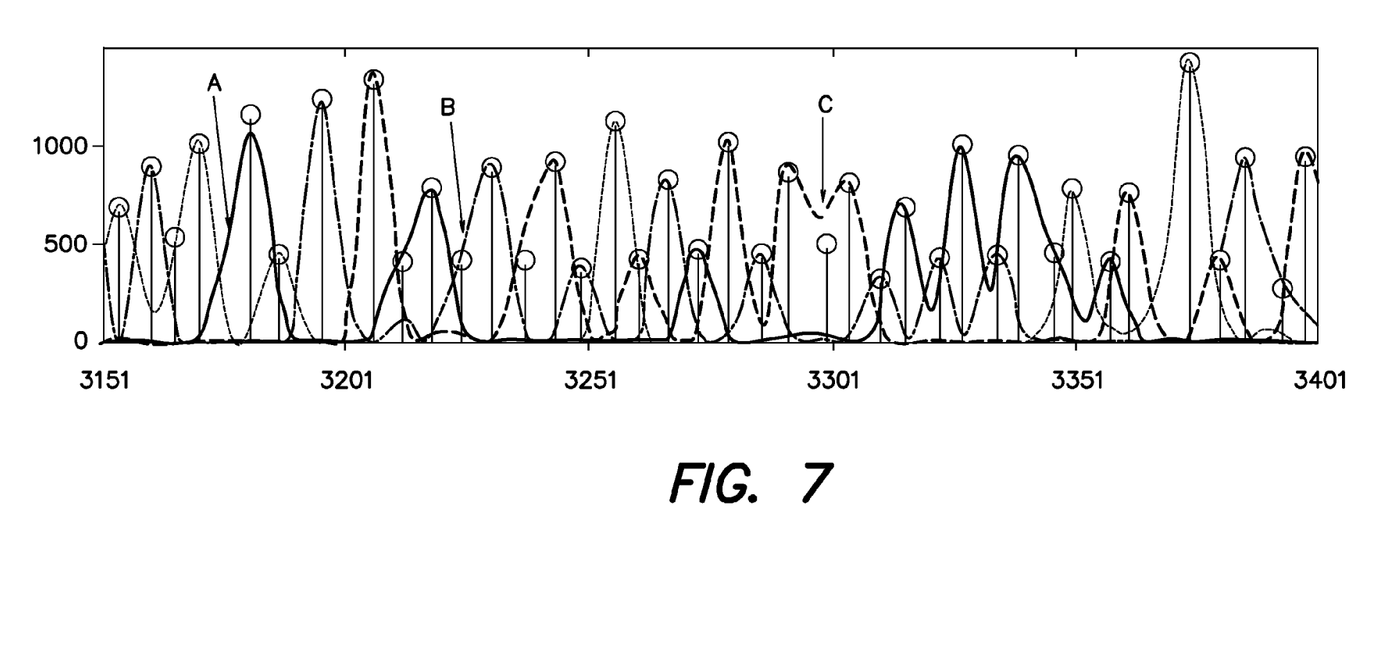
FIG. 7 illustrates an example of the deconvolved spike train for the composite trace portion shown in FIG. 2B.

FIG. 7 illustrates an example of the deconvolved spike train for the composite trace portion shown in FIG. 2B that results from computing the minimization expressed in equation 5. That is, each spike shows the amplitude ($\hat{\alpha}$) as a circle at a particular vertical line location ($\hat{\tau}$) in the time varying signal. It is noteworthy that the "hidden" pulses at around positions B and C are captured, while the minor peak to the left of position A has been missed. However, this does not necessarily mean that this will result in deletion in the final base call. This matter depends on whether the spike is counted as a single major peak, or overlapped major and minor peak in the second step, as described in further detail below.

It should be appreciated that because there is minimal prior information on the number of peaks in each window (i.e., $N_l$), the number is overestimated in minimizing equation 5. That is, the precise number of peaks $N_l$ for each window is not known a priori. However, the number can be estimated from observing empirical data, and particularly, the average number of peaks in a given window size may be approximated. This approximation may be increased to over-fit the data. The spikes identified by overfitting the data are either spikes that overlap the correct results, or noise spikes that are very low in amplitude. For the first case, overlapping spikes that are a distance of less than 1 time unit away may be combined. For the latter case, thresholding with a running average of peak amplitudes may eliminate some or all of the low amplitude noise spikes. Thus, having estimated the peak parameters for the composite trace, the first step is completed.

In the second step, the source of the identified peaks are determined. That is, the peaks identified in the first step are identified as either belonging to the major trace, the minor trace, both traces, or neither (i.e., the peak resulted from noise). As discussed above, the DNA sequencing reaction may be performed using reagent concentrations to control the amplitudes of the major and minor traces. Accordingly, the ratio between the trace amplitudes may be approximately known. For example, in some embodiments, the average trace amplitudes differ by a multiple of between 1.5 and 2.5. Let $\underline{\alpha}$, $\underline{\tau}$, $\underline{x}$ be estimated peak parameters for the overall data set, obtained by taking the union of the windowed parameters from step one. In some embodiments, the goal is to find, $$\hat{\underline{m}} = \arg\max_{\underline{m}} \log p(\underline{m} | \underline{\alpha}, \underline{\tau}, \underline{x}). \quad (6)$$

That is, the goal is to find the a posterior probability of the indicator variable $\underline{m}$, given the peak amplitudes ($\underline{\alpha}$) and peak locations ($\underline{\tau}$) computed in the first step, and the known base types $\underline{x}$. Equation 6 may operate as the global function to be factored and represented by a factor graph. To factor the global function, the distribution of peak amplitudes is assumed to be independent of the base type and peak location, and the superposition of the two spike trains is assumed dependent on only the peak locations, i.e., $p(\underline{\alpha}|\underline{m}, \underline{m}, \underline{\tau}, \underline{x}) = p(\underline{\alpha}|\underline{m})$, $p(\underline{m}|\underline{\tau}, \underline{x}) = p(\underline{m}|\underline{\tau})$. Therefore, equation 6 can be divided into two parts. The first part is related to the amplitude and the second part is related to the timing. Using Bayes rule and the above assumptions, equation 6 can be rewritten as, $$\hat{\underline{m}} = \arg\max_{\underline{m}} \left\{ \sum_k \log p(\alpha_k | m_k) + \log p(\underline{m} | \underline{\tau}) \right\}. \quad (7)$$

The dependency of the indicator m on α relates to the fact that the major and minor traces have different average amplitudes due to the reagent concentrations. That is, if $m_k$ is a major indicator it will be centered around an $\alpha_k$ indicative of the average amplitude of the major trace, if $m_k$ is a minor indicator it will be centered around an $\alpha_k$ indicative of the average amplitude of the minor trace, and if $m_k$ indicates both major and minor traces it will be centered around an $\alpha_k$ indicative of the sum of the average amplitudes of the major and minor traces. Accordingly, the first part of the expression relates the dependence of the indicator variable on amplitude.

To find the dependence of the indicator variable $\underline{m}$ on $\underline{\tau}$, it is observed that although the major and minor sequences are not synchronized, some uniformity of peak spacing is still maintained within each. That is, if the two sequences are offset slightly, then a peak identified as belonging to the major trace is more likely to be followed by a peak belonging to the minor trace and so on. Thus, m may be modeled as first order Markov, with transition probabilities determined by the timing difference, i.e., given $m_k$, the timing difference $\Delta\tau = \tau_{k+1} - \tau_k$ is assumed to determine the distribution of $m_{k+1}$. This assumption captures the dependence of the identity of each peak on the previous peak (i.e., the dependence of the indicator variable on timing). Accordingly, the second term in equation 7 can be expressed as, $$\log p(\underline{m} | \underline{\tau}) = \log p(m_1) + \sum_{k=2}^N \log p(m_k | m_{k-1}, \Delta\tau_k), \quad (8)$$

and equation 6 has thus been decomposed into summation terms, which can be used to generate a factor graph. It should be appreciated that a summation in the log probability domain is equal to a product in the probability domain. Let, $$R_k = p(\alpha_k \mid m_k), T_k = \begin{cases} p(m_k) & k = 1 \\ p(m_k \mid m_{k-1}, \Delta \tau_k) & k > 1. \end{cases} \quad (9)$$

Figure 8:
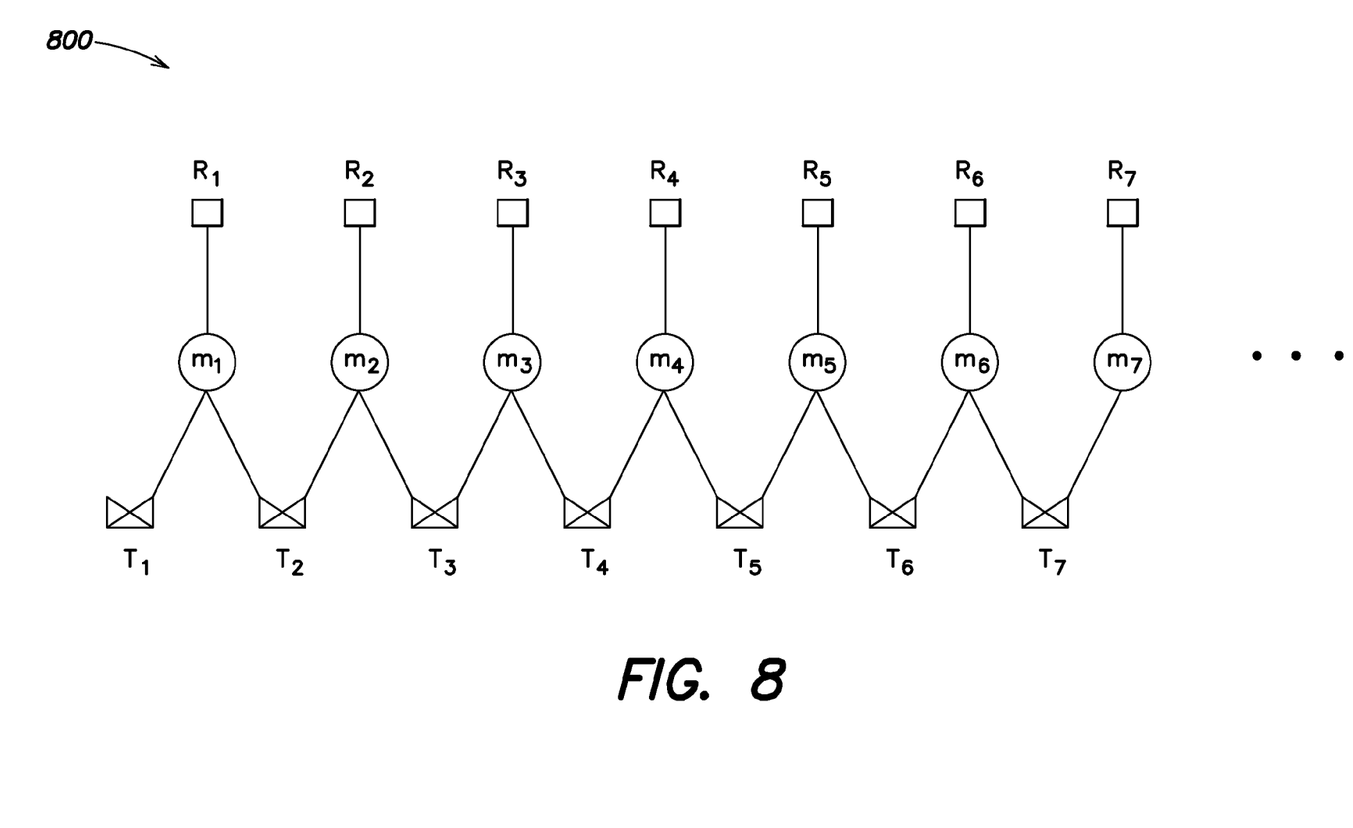
FIG. 8 illustrates a factor graph representation of the dependency of $\tilde{m}$ on the peak parameters.

Thus, $R_k$ is equal to the first term in equation 7, and $T_k$ equals the second term (which is comprised of the two components illustrated in equation 8). Thus, the global function in equation 6 can be rewritten as the product of $R_k$ and $T_k$. The global (objective) function has been factored into a product of local functions and can be represented as a factor graph. That is, the dependency of m on the peak parameters can therefore be represented graphically using a factor graph. FIG. 8 illustrates the factor graph representation of the dependency of m on the peak parameters The variables in the factor graph are the indicator variables $m_k$ for each set of peak parameters. As discussed above, the Sum-Product Algorithm can be applied to the factor graph to determine the marginal probabilities of each of the variables. That is, applying the Sum-Product algorithm to factor graph 800 results in the marginal distribution of each indicator variable m. From the marginal distribution, the maximum likelihood for each value of m can be determined and the solution to equation 6 can be computed to find the maximum likelihood estimate of m. Thus each parameter set is identified as either belonging to the major trace, the minor trace or both based on the maximum likelihood of the associated indicator variable as determined from the marginal distributions.

As discussed above, there are problems associated with using a full size factor graph (FG) for maximum a posterior (MAP) estimation of individual bases. By analyzing the estimator directly, Applicant has recognized that there may be simplifications that are possible. Assuming the additive noise is white, Gaussian, with zero mean and variance $\sigma^2$, the MAP estimator of the parameters are:

$$\hat{x}_1, \hat{\alpha}_1, \hat{\tau}_1, \hat{x}_2, \hat{\alpha}_2, \hat{\tau}_2 = \operatorname*{arg\,max}_{x_1, \alpha_1, \tau_1, x_2, \alpha_2, \tau_2} f(x_1, \alpha_1, \tau_1, x_2, \alpha_2, \tau_2 \mid y)$$

$$= \operatorname*{arg\,max}_{x_1, \alpha_1, \tau_1, x_2, \alpha_2, \tau_2} f(y \mid x_1, \alpha_1, \tau_1, x_2, \alpha_2, \tau_2)$$

$$f(x_1, \alpha_1, \tau_1, x_2, \alpha_2, \tau_2)$$

$$= \operatorname*{arg\,max}_{x_1, \alpha_1, \tau_1, x_2, \alpha_2, \tau_2}$$

$$\left\{ -\log\sqrt{2\pi}\,\sigma - \frac{1}{2\sigma^2} \sum_t \left\| y(t) - \sum_{i=1}^{N_1} \alpha_{1i} p(t - \tau_{1i}) x_{1i} + \sum_{j=1}^{N_2} \alpha_{2j} p(t - \tau_{2j}) x_{2j} \right\|^2 + \sum_{i=1}^{N_1} \log f(\alpha_{1i}) + \sum_{i=1}^{N_1} \log f(x_{1i}) + \log f(\tau_1, \tau_2) + \sum_{j=1}^{N_2} \log f(\alpha_{2j}) + \sum_{j=1}^{N_2} \log f(x_{2j}) \right\}$$

The above expression can be rewritten with a new set of variables $\hat{x}, \hat{\alpha}, \hat{\tau}, \hat{m}$, where $$\hat{x} = \{\hat{x}_1 \cup \hat{x}_2\}, \hat{\alpha} = \{\hat{\alpha}_1 \cup \hat{\alpha}_2\}, \hat{\tau} = \{\hat{\tau}_1 \cup \hat{\alpha}_2\}, m_k \in \{(00), (01), (11)\}.$$

Here the indicator variable $m_k$ is introduced and represents whether a peak at time $\tau_k$ has originated from noise, the major trace, the minor trace or both. If estimate values of $\alpha, x, \tau, m$ for each base could be estimated with high accuracy, the two constituent sequences can be identified. Assuming the amplitude and types of neighboring bases are independent, the MAP estimator can be rewritten with the new set of variables as:

$$\hat{x}, \hat{\alpha}, \hat{\tau}, \hat{m} =$$

$$\operatorname*{arg\,max}_{x, \alpha, \tau, m} \left\{ -\log\sqrt{2\pi}\,\sigma - \frac{1}{2\sigma^2} \sum_t \left\| y(t) - \sum_{k=1}^{N} \alpha_k p(t - \tau_k) x_k \right\|^2 + \sum_{k=1}^{N} \log f(\alpha_k \mid m) + \sum_{k=1}^{N} \log f(x_k \mid m) + \log f(\tau_1, \tau_2 \mid m) \right\}$$

Each of the four terms in the above expression can be analyzed to see whether simplifications are possible. First of all, the mean squared error fitting pulse trains to the data should be independent of the indicator variable associated with each base, since peak amplitude, location, and type already give sufficient information. For each individual base, it can be assumed that its amplitude is distributed independently of its neighbors. In other words, the only indicator variable affecting $\alpha_i$ is $m_i$. Similarly, since it is assumed that different types of bases occur uniformly, $x_i$ may be assumed independent of m for all i. On the other hand, since peak spacing is approximately first order Markov within a single sequence, once the union of $\tau_1$ and $\tau_2$ has been obtained, the dependency becomes at least second order. As a simple illustration, when the current base of interest is labeled as resulting from the major trace, if the previous base is labeled as resulting from both the major trace and the minor trace, then it is highly likely that these two peaks are distanced approximately by the average peak spacing. If instead the previous base is labeled as resulting from the minor trace, then the offset between these two peaks can be of any value up to the average peak spacing, while the offset between the current base and the one next to its immediate neighbor should be approximately the average peak spacing. This higher order Markov model of the peak spacing may be approximated by a first order model.

The MAP estimator can therefore be approximated as:

$$\hat{x}, \hat{\alpha}, \hat{\tau}, \hat{m} \simeq \operatorname*{arg\,max}_{x, \alpha, \tau, m} \left\{ \underbrace{-\log\sqrt{2\pi}\,\sigma - \frac{1}{2\sigma^2} \sum_t \left\| y(t) - \sum_{k=1}^{N} \alpha_k p(t - \tau_k) x_k \right\|^2}_{A(x, \alpha, \tau): \text{does not depend on } m} + \sum_{k=1}^{N} \log f(\alpha_k \mid m_k) + \underbrace{\sum_{k=1}^{N} \log f(x_k)}_{\text{assume uniform}} + \log f(\tau_1) + \underbrace{\sum_{k=2}^{N} \log f\left(\begin{array}{c}\tau_k \mid \tau_{k-1}, \\ m_k, m_{k-1}\end{array}\right)}_{\text{assume first order}} \right\} \quad (10)$$

$$= \operatorname*{arg\,max}_{x, \alpha, \tau, m} \{A(x, \alpha, \tau) + B(x, \alpha, \tau, m)\}$$

$$= \arg\max_{\underline{m}}\left\{\arg\max_{\underline{x},\underline{\alpha},\underline{\tau}}[A(\underline{x},\underline{\alpha},\underline{\tau}) + B(\underline{x},\underline{\alpha},\underline{\tau},\underline{m})]\right\}.$$

By expressing the cost function using two components as in Equation 10, a two stage algorithm for joint base-calling has essentially been derived: the first stage is to determine peaks for all possible indicator variables, and the second stage is to find the best indicator sequence to identify the source sequence for each peak. As a further simplification to solving the expression in Equation 1, a sub-optimal solution may be used wherein the sub-optimal solution is derived by neglecting the effect of $B(\underline{x}, \underline{\alpha}, \underline{\tau}, \underline{m})$ on the estimate of the peak parameters:

$$\hat{\underline{x}}, \hat{\underline{\alpha}}, \hat{\underline{\tau}} = \arg\max_{\underline{x},\underline{\alpha},\underline{\tau}} A(\underline{x},\underline{\alpha},\underline{\tau}). \tag{11}$$

$$\hat{\underline{m}} = \arg\max_{\underline{m}} B(\hat{\underline{x}}, \hat{\underline{\alpha}}, \hat{\underline{\tau}}, \underline{m}). \tag{12}$$

It should be noted that $A(\underline{x}, \underline{\alpha}, \underline{\tau})$ is similar in form to the cost function associated with a minimum mean square error estimator. Indeed, Equation 11 describes a deconvolution process, aiming at finding the minimum mean squared error estimate of the peak parameters. Equation 12, on the other hand, describes the MAP estimation of the indicator variable $\underline{m}$ given $\hat{\underline{x}}, \hat{\underline{\alpha}}, \hat{\underline{\tau}}$. This estimation may be carried out by using a factor graph.

To establish the desired FG, let us re-examine the expression for $B(\underline{x}, \underline{\alpha}, \underline{\tau}, \underline{m})$:

$$B(\underline{x},\underline{\alpha},\underline{\tau},\underline{m}) = \sum_{k=1}^{N}\log f(\alpha_k|m_k) + \underbrace{\sum_{k=1}^{N}\log f(x_k)}_{\text{assume uniform}} + \tag{13}$$

$$\underbrace{\log f(\tau_1) + \sum_{k=2}^{N}\log f(\tau_k|\tau_{k-1},m_k,m_{k-1})}_{\text{assume first order}}$$

$$= \sum_{k=1}^{N}\log f(\alpha_k|m_k) + \sum_{k=1}^{N}\log f(x_k) + \log f(\tau_1) +$$

$$\sum_{k=2}^{N}\log\underbrace{\frac{f(m_k|\tau_k,\tau_{k-1},m_{k-1})f(\tau_k|\tau_{k-1},m_{k-1})}{f(m_k|\tau_{k-1},m_{k-1})}}_{\approx \log f(m_k|\Delta\tau_k,m_{k-1})}.$$

$$= \sum_{k=1}^{N}\log f(\alpha_k|m_k) + \sum_{k=1}^{N}\log f(x_k) + \log f(\tau_1) + \tag{14}$$

$$\sum_{k=2}^{N}\log f(m_k|\Delta\tau_k,m_{k-1}).$$

It should be noted that $B(\underline{x}, \underline{\alpha}, \underline{\tau}, \underline{m})$ can be further divided into three parts, each associated with a different peak parameter. To better differentiate the major and minor traces, it may be more desirable to resolve the peak amplitude distributions for the two traces as much as possible, although a relatively significant average peak amplitude for the minor trace is still desirable to maintain the signal to noise ratio (e.g., to accurately distinguish peaks in the minor trace from noise). Also, the number of bases coming from each base type may be assumed to be the same. It is known that in some special cases, more prior information on the base type distribution is available, depending on the organism or the gene being sequenced, such that the distribution of x becomes non-uniform.

Moreover, the inter-dependencies of the peak locations and the indicator variables have been simplified from Equation 13 to Equation 14, such that $\underline{m}$ becomes first order Markov when the difference in peak locations is given. An example of $\underline{m}$ being first order Markov is the case where a first peak is from the major trace and the next peak is approximately half the average peak distance away, wherein it can be concluded that with relatively high probability that the next sequence is from the minor trace. Let, $$R_k = f(\alpha_k|m_k), T_k = \begin{cases} f(\tau_k) & k=1 \\ f(m_k|m_{k-1},\Delta\tau_k) & k>1 \end{cases}$$

The factor graph for the MAP estimation of the indicator variable may thus be constructed as illustrated in FIG. 8. In applying the sum-product algorithm, the messages from variable nodes to function nodes are:

$$\mu R_k \rightarrow m_k = R_k$$

$$\mu m_k \rightarrow T_k = \mu R_k \rightarrow m_k \cdot \mu T_{k+1} \rightarrow m_k$$

$$\mu m_k \rightarrow T_{k+1} = \mu R_k \rightarrow m_k \cdot \mu T_k \rightarrow m_k$$

Messages from function nodes to variable notes (k>1) are:

$$\mu_{T_k \rightarrow m_{k-1}} = \sum_{\sim m_{k-1}} T_k \mu_{m_k \rightarrow T_k} = \sum_{m_k} p(m_k|m_{k-1},\Delta_{\tau_k})\mu_{m_k \rightarrow T_k}$$

$$\mu_{T_k \rightarrow m_k} = \sum_{\sim m_k} T_k \mu_{m_{k-1} \rightarrow T_k} = \sum_{m_{k-1}} p(m_k|m_{k-1},\Delta_{\tau_k})\mu_{m_{k-1} \rightarrow T_k}$$

Recall that it has been tried to simplify the conditional distribution of the peak parameters to be first order, i.e., those for one peak depends on only those for its immediate neighbor. Such simplifications facilitate relatively easy computation, but a second order model may be more appropriate in some circumstances. A possible second order approximation to the joint distribution of $\underline{\tau}_1$ and $\underline{\tau}_2$ is:

$$\log f(\underline{\tau}_1, \underline{\tau}_2) = \log f(\underline{\tau}|\underline{m})$$

$$= \log f(\tau_1, \tau_2) + \sum_{k=3}^{N} \log f\begin{pmatrix} \tau_k|\tau_{k-1}, \tau_{k-2}, m_k, \\ m_{k-1}, m_{k-2} \end{pmatrix},$$

Where $$\log f\begin{pmatrix} \tau_k|\tau_{k-1}, \tau_{k-2}, \\ m_k, m_{k-1}, m_{k-2} \end{pmatrix} = \tag{15}$$

$$\begin{cases} \log f_T(\tau_k - \tau_{k-1}) & m_{k-1} = 11 \\ \log f_T(\tau_k - \tau_{k-2}) & (m_{k-2}, m_k) = (11, 11) \\ & \text{or } m_j \neq 11, k-2 \leq j \leq k \\ \log f_T\left(\tau_k - \frac{1}{2}(\tau_{k-1} + \tau_{k-2})\right) & m_{k-2} \neq 11, m_{k-1} \neq 11, m_k = 11. \end{cases}$$

Figure 9:
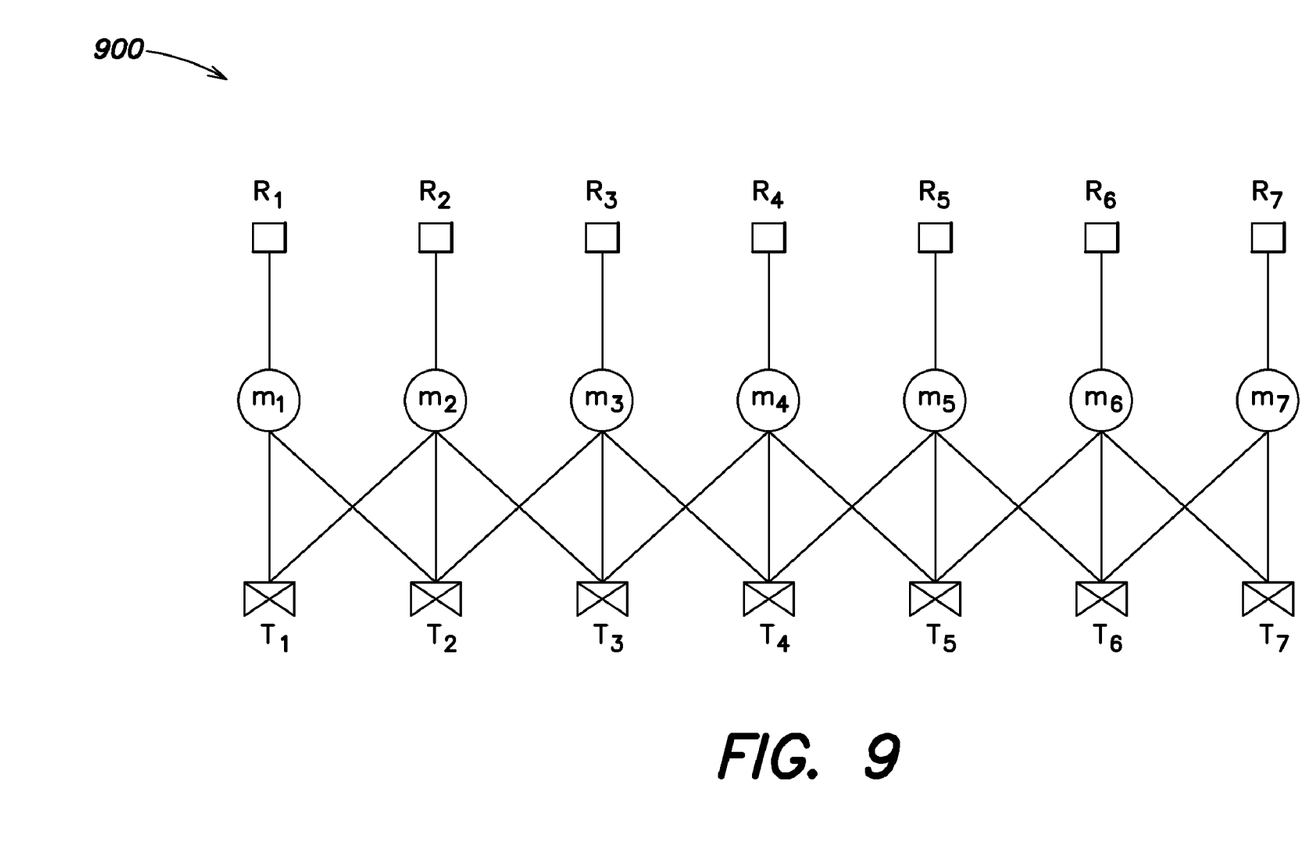
FIG. 9 illustrates a factor graph representation of a second order function.

Again using $R_k$ and $T_k$ to represent the conditional probabilities, the alternative factor graph is illustrated in FIG. 9 and the Sum-Product algorithm can be applied to determine probabilities.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed function. The one or more controller can be implemented in numerous ways, such as with dedicated hardware, or with general purpose hardware (e.g., one or more processor) that is programmed using microcode or software to perform the functions recited above.

It should be appreciated that the various methods outlined herein may be coded as software that is executable on one or more processors that employ any one of a variety of operating systems or platforms. Additionally, such software may be written using any of a number of suitable programming languages and/or conventional programming or scripting tools, and also may be compiled as executable machine language code.

In this respect, it should be appreciated that some embodiment are directed to a computer readable medium (or multiple computer readable media) (e.g., a computer memory, one or more floppy discs, compact discs, optical discs, magnetic tapes, etc.) encoded with one or more programs that, when executed on one or more computers or other processors, perform methods that implement the various embodiments discussed above. The computer readable medium or media can be transportable, such that the program or programs stored thereon can be loaded onto one or more different computers or other processors to implement various aspects as discussed above.

It should be understood that the term "program" is used herein in a generic sense to refer to any type of computer code or set of instructions that can be employed to program a computer or other processor to implement various aspects as discussed above. Additionally, it should be appreciated that according to one aspect of this embodiment, one or more computer programs need not reside on a single computer or processor, but may be distributed in a modular fashion amongst a number of different computers or processors to implement various aspects described herein.

Various embodiments may be used alone, in combination, or in a variety of arrangements not specifically discussed in the embodiments described in the foregoing and is therefore not limited in its application to the details and arrangement of components set forth in the foregoing description or illustrated in the drawings.

Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

What is claimed is:

1. A computer readable medium having processor-executable instructions stored thereon, the processor-executable instruction, when executed by at least one processor, performing a method of automated base-calling using at least one image obtained from a chemical sequencing process performed simultaneously on a plurality of DNA strands, the at least one image including intensity information corresponding to locations of at least one base in the plurality of DNA strands, the method comprising:

processing the at least image to obtain a function corresponding to the intensity information in the at least one image for the at least one base, the function incorporating intensity information corresponding to each of the plurality of DNA strands;

identifying a plurality of peaks in the function, the plurality of peaks indicating possible locations for the at least one base in the plurality of DNA strands;

assigning membership to each of the plurality of peaks by determining whether each of the plurality of peaks is believed to have resulted from none, one or multiple of the plurality of DNA strands; and computing a sequence for the at least one base for each of the plurality of DNA strands based, at least in part, on the membership assignment.

2. The computer readable medium of claim 1, wherein the at least one image includes sequence information for four different bases for the plurality of DNA strands, and wherein processing the at least one image includes obtaining a function for each of the four bases, each function comprising intensity information from each of the plurality of DNA strands for respective ones of the four different bases.

3. The computer readable medium of claim 2, wherein identifying the plurality of peaks includes identifying a plurality of peaks in each function, and wherein computing a sequence includes computing a sequence indicating the sequence of the four bases for the plurality of DNA strands.

4. The computer readable medium of claim 2, wherein the plurality of DNA strands includes a first DNA strand and a second DNA strand such that the at least one image records intensity information for a dual chemical sequencing process, wherein the function includes the superposition of information from the first DNA strand and the second DNA strand, and wherein assigning membership to each of the plurality of peaks includes determining whether each of the plurality of peaks belongs to none, the first DNA strand, the second DNA strand or both the first DNA strand and the second DNA strand.

5. The computer readable medium of claim 4, wherein each function simultaneously represents a major trace having peaks associated with the first DNA strand and a minor trace having peaks associated with the second DNA strand for respective ones of the four bases, and wherein assigning membership includes differentiating the plurality of peaks as belonging to the major trace, the minor trace, both the major trace and the minor trace or neither the major trace or the minor trace.

6. The computer readable medium of claim 5, wherein computing includes computing a sequence of the four bases for the first DNA strand and the second DNA strand.

7. The computer readable medium of claim 1, wherein the chemical sequencing process applies a different concentration of reagent to each of the plurality of strands during the chemical sequencing process so that the average peak intensity for peaks arising from each of the plurality of DNA strands are different, and wherein the function comprises a superposition of the intensity information from the plurality of DNA strands.

8. The computer readable medium of claim 1, wherein identifying a plurality of peaks comprises estimating peak amplitudes and peak locations in the function, and wherein assigning membership comprises determining a probability that each of the plurality of peaks resulted from none, one or multiple DNA strands based, at least in part, on the peak amplitudes and peak locations.

9. The computer readable medium of claim 8, wherein determining the probability includes factoring the function into a factor graph and traversing the factor graph to determine the probability that each of the plurality of peaks resulted from none, one or multiple DNA strands based, at least in part, on the peak amplitudes and peak locations.

10. The computer readable medium of claim 9, wherein traversing the factor graph includes applying a Sum-Product algorithm to the factor graph to determine the probability that each of the plurality of peaks resulted from none, one or multiple DNA strands based, at least in part, on the peak amplitudes and peak locations.

11. An apparatus for performing automated base-calling using at least one image obtained from a chemical sequencing process performed simultaneously on a plurality of DNA strands, the at least one image including intensity information corresponding to locations of at least one base in the plurality of DNA strands, the apparatus comprising:
    an input to receive the at least one image; and
    at least one controller configured to process the at least image to obtain a function corresponding to the intensity information in the at least one image for the at least one base, the function incorporating intensity information corresponding to each of the plurality of DNA strands, identify a plurality of peaks in the function, the plurality of peaks indicating possible locations for the at least one base in the plurality of DNA strands, assigning membership to each of the plurality of peaks by determining whether each of the plurality of peaks is believed to have resulted from none, one or multiple of the plurality of DNA strands, and compute a sequence for the at least one base for each of the plurality of DNA strands based, at least in part, on the membership assignment.

12. The apparatus of claim 11, wherein the at least one image includes sequence information for four different bases for the plurality of DNA strands, and wherein the controller is configured to obtain a function for each of the four bases, each function comprising intensity information from each of the plurality of DNA strands for respective ones of the four different bases.

13. The apparatus of claim 12, wherein the controller is configured to identify a plurality of peaks in each function, and compute a sequence indicating the sequence of the four bases for the plurality of DNA strands.

14. The apparatus of claim 12, wherein the plurality of DNA strands includes a first DNA strand and a second DNA strand such that the at least one image records intensity information for a dual chemical sequencing process, wherein the function includes the superposition of information from the first DNA strand and the second DNA strand, and wherein the controller is configured to determine whether each of the plurality of peaks belongs to none, the first DNA strand, the second DNA strand or both the first DNA strand and the second DNA strand.

15. The apparatus of claim 14, wherein each function simultaneously represents a major trace having peaks associated with the first DNA strand and a minor trace having peaks associated with the second DNA strand for respective ones of the four bases, and wherein the controller is configured to differentiate the plurality of peaks as belonging to the major trace, the minor trace, both the major trace and the minor trace or neither the major trace or the minor trace.

16. The apparatus of claim 15, wherein the controller is configured to compute a sequence of the four bases for the first DNA strand and the second DNA strand.

17. The apparatus of claim 11, wherein the chemical sequencing process applies a different concentration of reagent to each of the plurality of strands during the chemical sequencing process so that the average peak intensity for peaks arising from each of the plurality of DNA strands are different, and wherein the function comprises a superposition of the intensity information from the plurality of DNA strands.

18. The apparatus of claim 11, wherein the controller is configured to estimate peak amplitudes and peak locations in the function, and determine a probability that each of the plurality of peaks resulted from none, one or multiple DNA strands based, at least in part, on the peak amplitudes and peak locations.

19. The apparatus of claim 18, wherein the controller is configured to determine the probability by factoring the function into a factor graph and traversing the factor graph to determine the probability that each of the plurality of peaks resulted from none, one or multiple DNA strands based, at least in part, on the peak amplitudes and peak locations.

20. The apparatus of claim 19, wherein the controller is configured to apply a Sum-Product algorithm to the factor graph to determine the probability that each of the plurality of peaks resulted from none, one or multiple DNA strands based, at least in part, on the peak amplitudes and peak locations.

* * * * *